(12) United States Patent
McCall et al.

(10) Patent No.: US 7,527,077 B2
(45) Date of Patent: May 5, 2009

(54) MULTI-PHASE PERSONAL CARE COMPOSITIONS, PROCESSES FOR MAKING AND PROVIDING, AND ARTICLES OF COMMERCE

(75) Inventors: Patrick Columkille McCall, Loveland, OH (US); Robert Lee Wells, Cincinnati, OH (US); Bryan Gabriel Comstock, Mason, OH (US); Michael Frederick Niebauer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/067,443

(22) Filed: Feb. 25, 2005

(65) Prior Publication Data

US 2006/0191589 A1    Aug. 31, 2006

(51) Int. Cl.
    *B65B 1/04*    (2006.01)
(52) U.S. Cl. .................................... 141/9; 141/2
(58) Field of Classification Search .............. 141/2, 141/18, 989, 100, 104; 222/1, 144.5
    See application file for complete search history.

(56) References Cited

U.S. PATENT DOCUMENTS

| | | | |
|---|---|---|---|
| 3,479,429 A | 11/1969 | Morshauser et al. | |
| 3,533,955 A | 10/1970 | Pader et al. | |
| 3,937,811 A | 2/1976 | Papantoniou et al. | |
| 4,159,028 A * | 6/1979 | Barker et al. ................. | 141/9 |
| 4,263,363 A | 4/1981 | Buck et al. | |
| 4,335,103 A | 6/1982 | Barker | |
| 4,425,322 A | 1/1984 | Harvey et al. | |
| 4,518,578 A | 5/1985 | Hayes et al. | |
| 4,786,449 A * | 11/1988 | Smit ............................ | 264/73 |
| 4,966,205 A * | 10/1990 | Tanaka ......................... | 141/9 |
| 4,980,155 A | 12/1990 | Shah et al. | |
| 5,059,414 A | 10/1991 | Dallal | |
| 5,228,912 A | 7/1993 | Driller et al. | |
| 5,393,450 A | 2/1995 | Shana'a et al. | |
| 5,455,035 A | 10/1995 | Guerrero et al. | |
| 5,487,168 A | 1/1996 | Geiner et al. | |
| 5,556,628 A | 9/1996 | Derian et al. | |
| 5,612,307 A | 3/1997 | Chambers et al. | |
| 5,635,171 A | 6/1997 | Nadaud et al. | |
| 5,661,189 A | 8/1997 | Grievson et al. | |
| 5,851,978 A | 12/1998 | Shana'a | |
| 5,903,465 A * | 5/1999 | Brown ......................... | 700/242 |
| 5,929,019 A | 7/1999 | Puvvada et al. | |
| 5,947,335 A | 9/1999 | Milio et al. | |
| 5,952,286 A | 9/1999 | Puvvada et al. | |
| 5,965,500 A | 10/1999 | Puvvada | |
| 5,993,792 A * | 11/1999 | Rath et al. ................... | 424/70.28 |
| 6,174,845 B1 | 1/2001 | Rattinger et al. | |
| 6,176,391 B1 | 1/2001 | Rehkemper et al. | |
| 6,176,395 B1 | 1/2001 | Abbott et al. | |
| 6,190,648 B1 | 2/2001 | Kouzu et al. | |
| 6,213,166 B1 | 4/2001 | Thibiant et al. | |
| 6,245,323 B1 | 6/2001 | Christie et al. | |
| 6,245,344 B1 | 6/2001 | Thibiant | |
| 6,268,322 B1 | 7/2001 | St. Lewis et al. | |
| 6,306,806 B1 | 10/2001 | St. Lewis et al. | |
| 6,340,723 B1 | 1/2002 | Nita et al. | |
| 6,367,519 B2 | 4/2002 | Thibiant et al. | |
| 6,383,999 B1 | 5/2002 | Coyle et al. | |
| 6,429,177 B1 | 8/2002 | Salmon et al. | |
| 6,506,391 B1 | 1/2003 | Biatry | |
| 6,516,838 B2 | 2/2003 | Thibiant et al. | |
| 6,517,939 B1 | 2/2003 | Ramin et al. | |
| 6,534,456 B2 | 3/2003 | Hayward et al. | |
| 6,534,457 B2 | 3/2003 | Mitra | |
| 6,673,755 B2 | 1/2004 | Wei et al. | |
| 6,695,510 B1 * | 2/2004 | Look et al. ..................... | 401/68 |
| 6,935,386 B2 * | 8/2005 | Miller et al. .................. | 141/18 |
| 7,082,970 B2 * | 8/2006 | Bartholomew et al. ...... | 141/104 |
| 2001/0036467 A1 | 11/2001 | Thibiant | |
| 2002/0004468 A1 | 1/2002 | Hodge et al. | |
| 2002/0010110 A1 | 1/2002 | Hayward | |
| 2002/0136700 A1 * | 9/2002 | Margosiak et al. ......... | 424/70.21 |
| 2003/0111130 A1 | 6/2003 | Dugdale | |
| 2003/0152540 A1 | 8/2003 | Putman et al. | |
| 2003/0161852 A1 | 8/2003 | Miller et al. | |
| 2003/0180246 A1 | 9/2003 | Frantz et al. | |
| 2003/0222100 A1 | 12/2003 | Husband et al. | |
| 2004/0004309 A1 * | 1/2004 | Sears .......................... | 264/325 |
| 2004/0048757 A1 | 3/2004 | Zhang et al. | |

(Continued)

FOREIGN PATENT DOCUMENTS

CA    2246316    6/1998

(Continued)

OTHER PUBLICATIONS

XP 002332778 "Dove All Day Moisturizing Body Wash" Online URL: http://www.ewg.org/reports/skindeep2/report.php?type=PRODUCT&id=8801874.

(Continued)

*Primary Examiner*—Steven O Douglas
(74) *Attorney, Agent, or Firm*—Laura R. Grunzinger; Melody A. Jones

(57) ABSTRACT

A multi-liquid phase composition wherein said phases are visually distinctive. These compositions combine multiple phases for creating personal care compositions.

2 Claims, No Drawings

U.S. PATENT DOCUMENTS

| | | |
|---|---|---|
| 2004/0048758 A1 | 3/2004 | Zhang et al. |
| 2004/0057920 A1 | 3/2004 | Focht et al. |
| 2004/0092415 A1 | 5/2004 | Focht et al. |
| 2004/0105827 A1 | 6/2004 | Grimm et al. |
| 2004/0158940 A1 | 8/2004 | Wells et al. |
| 2004/0219119 A1 | 11/2004 | Wei et al. |
| 2004/0223929 A1 | 11/2004 | Clapp et al. |
| 2004/0223939 A1 | 11/2004 | Clapp et al. |
| 2004/0223991 A1 | 11/2004 | Wei et al. |
| 2004/0235693 A1 | 11/2004 | Wei et al. |
| 2004/0242706 A1 | 12/2004 | Wiersema et al. |
| 2004/0245263 A1* | 12/2004 | Bartholomew et al. ......... 221/1 |
| 2004/0248748 A1 | 12/2004 | Wei |
| 2005/0020468 A1 | 1/2005 | Frantz et al. |
| 2005/0100570 A1 | 5/2005 | Wei et al. |
| 2005/0143269 A1 | 6/2005 | Wei et al. |
| 2005/0192187 A1 | 9/2005 | Wagner et al. |
| 2005/0192188 A1 | 9/2005 | Wagner et al. |
| 2005/0192189 A1 | 9/2005 | Wagner et al. |
| 2005/0238680 A1 | 10/2005 | Stella et al. |
| 2005/0250658 A1 | 11/2005 | Putman |
| 2005/0276768 A1 | 12/2005 | Wei et al. |
| 2006/0002880 A1 | 1/2006 | Peffly et al. |

FOREIGN PATENT DOCUMENTS

| | | |
|---|---|---|
| DE | 196 50 952 A | 6/1998 |
| DE | 198 54 086 A | 5/2000 |
| EP | 0 078138 A2 | 5/1983 |
| EP | 0 331617 B | 4/1992 |
| EP | 1 108421 A2 | 6/2001 |
| EP | 1 005849 B1 | 9/2001 |
| EP | 1 064918 B1 | 9/2002 |
| EP | 0 907345 B1 | 5/2003 |
| GB | 1277324 A | 6/1972 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A1 | 1/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2005/067875 A1 | 7/2005 |

OTHER PUBLICATIONS

XP002332779 "Olay Daily Renewal Moisturizing Body Wash" Online URL: http://householdprdoucts.nlm.nih.gov/cgi-bin/household.brands?tbl=brands&id=16003084.

* cited by examiner

MULTI-PHASE PERSONAL CARE COMPOSITIONS, PROCESSES FOR MAKING AND PROVIDING, AND ARTICLES OF COMMERCE

FIELD OF THE INVENTION

The invention relates to stable, visually distinctive multi-phase liquid compositions, processes for making and providing such compositions, and articles of commerce comprising such compositions.

BACKGROUND OF THE INVENTION

Under the time pressures of daily life, individuals are seeking more efficient ways to address personal hygienic needs. For example, two-in-one shampoos that cleanse and condition in a single step are widely used by the consuming public. This same convenience is sought by consumers in the form of skin cleansing products that clean like bar soap, but also condition the skin. Likewise, consumers seek skin creams, lotions, and other such compositions that can deliver more than one consumer-desired benefit. Furthermore, consumers seek products that not only provide at least one personal care benefit, but also have an aesthetically pleasing appearance, thus enhancing the consumer's enjoyment of product use.

Early attempts at providing such products employed dual-chamber packaging containing, for example, separate cleansing and conditioning products. The separate conditioning and cleansing compositions remain physically separate and stable during prolonged storage. These packages were designed to co-dispense the products together to effectuate simultaneous cleaning and conditioning. In another embodiment, the cleaning and conditioning products are mixed just prior to dispensing. Although such dual-chamber delivery systems seemed to provide the improved convenience sought by consumers, they frequently failed to achieve consistent and uniform performance because of the uneven dispensing of the different phases that can be inherent in such a dual-chamber system. This also often led to consumer frustration, as one chamber would be emptied through use long before the other chamber was exhausted, resulting in wasted, unused product. Additionally, these packaging systems add considerable cost to the finished product and tended to be obtrusive in areas such as usual home tub/showers.

Alternatively, compositions comprising two visually distinct phases were combined in typical, top-dispensing (e.g., pump, jar, bottle) product packaging for simultaneous dispensing of both phases. These products required special processing wherein two initially separate and distinct phase compositions are channeled to a filling head and simultaneously dispensed into a rotating package or container. Stirring the product in the filling head during packaging is achieved by using a plurality of stirring rods disposed about the filling head. These products, while having a visually attractive "spiral" appearance in the container before use, can easily lose their attractiveness once the product is used. For instance, as the bottle is turned upside-down and squeezed to dispense product through the bottle orifice, then turned up-right again for storage, the product's initially-attractive multi-phased appearance can be disrupted by the movement of an air bubble throughout the product as the product is turned upside-down then back to up-right position. This leads to a product that quickly loses the desired aesthetic appearance, thus detracting from the consumer's usage experience. Furthermore, the same pattern disruption can occur during transport of the product from manufacturing facility to the consumer point of purchase, thus resulting in products having an undesirable appearance even before use.

On the basis of the discussion above, there still remains a need for making a single product that dispenses from routine packaging, yet maintains its desired multi-phase appearance.

BACKGROUND ART

The following references relate to multiple liquid phase packaging: U.S. Pat. No. 4,159,028, issued Jun. 26, 1979, in the name of Barker et al.: U.S. Pat. No. 4,335,103, issued Jun. 15, 1982, in the name of Barker et al.; U.S. Pat. No. 6,245,344, issued Jun. 12, 2001 in the name of Thibiant et al.; U.S. Pat. No. 6,367,519, issued Apr. 9, 2002, in the name of Thibiant et al.; U.S. Pat. No. 6,516,838, issued Feb. 11, 2003, in the name of Thibiant et al.

SUMMARY OF THE INVENTION

The invention relates to a personal care composition comprising a plurality of visually distinctive phases wherein the phases remain visually stable in the product container. Furthermore, the invention relates to a method for making and providing such a product.

In one embodiment, the process for making a stable, visually distinct, multiple liquid phase composition comprises the steps of:

a. placing a plurality of liquid compositions in separate vessels equipped with at least one dispensing means for transferring said compositions from said vessels, wherein said liquid compositions are physically distinct from one another;

b. providing an empty product container, wherein said empty product container is a tottle;

c. filling said empty product container with said liquid compositions to form a container of said personal care composition having a void volume of from about 0% to about 4%, wherein said filling step comprises transferring predetermined amounts of said liquid compositions through at least one said dispensing means into said empty product container; and d. optionally curing said personal care composition, wherein said curing step optionally comprises maintaining said product container in the same orientation in which it was filled until the desired level of cure is reached.

In one embodiment, the product container is a bottle that is filled from the same end from which the product is to be dispensed. In a particular embodiment, the end from which the bottle is filled is not only the end from which the product is to be dispensed, but it is also the end upon which the bottle is intended to rest or sit upon (e.g., the bottle's base) for storage by the consumer and/or for display on the store shelf (this bottle is referred to herein as a "tottle").

In a particular embodiment, this process further involves initially placing the nozzle near the bottom of the container to be filled and lifting the nozzle as the container fills. Additionally, during filling, the container can be secured on a rotating platform for rotating the bottle while being filled. The platform can be rotated at speeds to provide an appropriate pattern of the composition to provide the aesthetic benefit mentioned above. Typical platform speeds range from about 0 revolutions per minute (rmp) to 800 rmp. If desired, the rotating platform can be rotated by a variable speed drive mechanism.

In one embodiment of this process, the pattern comprises phases that are visually distinct from each other. The visual distinction between the phases can be in color or texture. The specific pattern can be chosen from a wide variety of patterns, including, but not limited to striping, marbling, geometrics, spirals, and mixtures thereof.

In another aspect, the present invention provides a method for providing said composition. This method comprises the steps of:
a. placing a plurality of liquid compositions in separate vessels equipped with at least one dispensing means for transferring said compositions from said vessels, wherein said liquid compositions are physically distinct from one another;
b. providing an empty product container, wherein said empty product container is a tottle;
c. filling said empty product container with said liquid compositions to form a container of said personal care composition having a void volume of from about 0% to about 4%, wherein said filling step comprises transferring predetermined amounts of said liquid compositions through at least one said dispensing means into said empty product container;
d. optionally curing said personal care composition, wherein said curing step optionally comprises maintaining said product container in the same orientation in which it was filled until the desired level of cure is reached; and
e. placing said container in a shipping package, wherein said container is placed in said shipping package in the same orientation at which it was filled.

In another aspect, the present invention provides an article of commerce, wherein said article comprises:
a. a bottle; and
b. a personal care composition contained within said bottle, wherein said personal care composition comprises at least two physically distinct phases, and further wherein said personal care composition has an average low shear rate viscosity of from about 25 to about 2000 Pascal-seconds in at least one phase.

In a particular embodiment, the personal care composition has an average low shear rate viscosity of from about 50 to about 1500 Pascal-seconds, and in still another embodiment the personal care composition has an average low shear rate viscosity of from about 75 to about 1000 Pascal-seconds.

In one embodiment, the physically distinct phases comprise phases that are visually distinct from each other. The visual distinction between the phases can be in color or texture. The specific pattern can be chosen from a wide variety of patterns, including, but not limited to striping, marbling, geometries, spirals, and mixtures thereof.

Definitions

The term "ambient conditions" as used herein, unless otherwise specified, refers to surrounding conditions at one (1) atmosphere of pressure, 50% relative humidity, and 25° C.

The term "stable" as used herein, unless otherwise specified, refers to compositions that maintain visually distinctive phases in physical contact at ambient conditions for a period of at least about 30 days, without agitation.

The term "personal care composition" as used herein, unless otherwise specified, refers to the compositions of the present invention, wherein the compositions are intended to include compositions for topical application to the skin or hair. Such personal care compositions can include, but are not limited to, shampoos, conditioners, hair styling products, cleansers, soaps, cosmetics, foundations, antiperspirants, deodorants, lotions, creams, ointments, combinations thereof, and the like.

The term "phase" as used herein refers to a homogeneous, physically distinct, and mechanically separable portion of matter present in a non-homogeneous physical-chemical system. In some embodiments, the phases herein are compositions with different colors. In some embodiments, the phases comprise the same chemical compositions but with different colorants.

The term "visually distinctive" or "visually distinct" as used herein describes compositions in the package or upon being dispensed that display visually different phases. These different phases are either distinctively separate or partially mixed as long as the multiple liquid phase composition remains visible to the naked eye.

The term "stripe" as used herein means that each phase present in the composition occupies separate but distinct physical spaces inside the package in which it is stored, but are in direct contact with one another. In one preferred embodiment of the present invention, a personal care composition comprises at least two phases that are present within the container as distinct layers or "stripes". The stripes may be relatively uniform and even across the dimension of the package. Alternatively the layers may be uneven, i.e. wavy, or may be non-uniform in dimension. The stripes do not necessarily extend across the entire dimension of the package. The "stripe" can comprise various geometric patterns, various colors and, or glitter or pearlescence, providing that the concentration of said alternative forms visually distinct bands or regions.

The term "marbling" as used herein refers to a striped design with a veined and/or mottled appearance similar to marble.

The methods defined below allow quantitative measurement of the striped and marbled patterns utilized in the compositions comprising multiple liquid phases of the instant application:

1. Method for Measuring Average Stripe Size (AS)

First, a vertical line is drawn along the center of the product package using a pencil. Total the number of visually distinctive product stripes or N, including all product stripes with varying colors. Divide the height of the product package is measured as D in millimeters mm) by N. The average stripe size is calculated as:

$$AS=D/N$$

The average stripe size (AS) in one embodiment of the present invention is about 0.1 mm to about 10 mm, in another embodiment from about 0.5 mm to about 5 mm, and in another embodiment from about 0.5 mm to about 2 mm.

2. Color Method for Striped/Marbled Multiple liquid phase Compositions

The GretagMacbeth Color-Eye 70000A spectrophotometer is used to measure color difference of striped/marbled multiple liquid phase compositions. The aperture size is 3 mm by 8 mm (Very Small Area of View). The instrument is running at reflectance mode with 2° incident light beam. First, one color measurement is made around the lightest area of the sample. This reading is used as the color standard. A second color measurement is made around the darkest area of the sample. This color reading is compared to the color standard (light spot) and color difference is computed as $\Delta E$.

The striped/marbled multiple liquid phase compositions in the present invention have $\Delta E \geq 1$. Preferably, $\Delta E$ is greater than 2. Most preferably, $\Delta E$ is greater than 4.

3. Viscosity of the Personal Care Composition

The Wells-Brookfield Cone/Plate Model DV-II+ Viscometer is used to determine the viscosity of the liquid personal care compositions herein. The determination is performed at 25 C with the 2.4 cm$^0$ cone measuring system with a gap of 0.013 mm between the two small pins on the respective cone and plate. The measurement is performed by injecting 0.5 ml of the sample to be analyzed between the cone and plate and setting the cone at a set speed of 1 rpm. The resistance to the rotation of the cone produces a torque that is proportional to the shear stress of the liquid sample. The amount of torque is read 2 minutes after loading the sample and computed by the viscometer into absolute centipoise units (mPa*s) based on the geometric constant of the cone, the rate of rotation, and the stress related torque.

Average Low Shear Rate of Liquid Personal Cleansing Composition

The AR 2000 Rheometer, available from TA Instruments of New Castle, Del., USA, is used to determine the average low shear rate viscosity of the liquid personal cleansing compositions. For purpose herein, the average low shear rate viscosity is determined by computing the average of the viscosities over a range of 0.0005 l/s to 0.005 l/s. The determination is performed at 25 C with the 4 cm 2$^0$ cone (truncated to 53 microns) measuring system set with a 53 micron gap. The determination is performed via the programmed application of a logarithmic shear stress ramp (typically from about 0.05 Pascals to about 500 Pascals) over time interval of 4 minutes.

Void Volume of Personal Care Compositions

The void volume left in a package after the completion of the filling and capping operations is determined as follows:

1. Take a representative sampling of packages and closures, filling the package (manually if need be) with 25 C water up to the point of overflow, and cap with the closures, drying off any water that is displaced. Record an average weight.
2. For the same package and closure, obtain an average weight of empty and dry package and closure.
3. Fill a representative number of packages with the intended composition, preferably de-aerated, capping with closures. Obtain an average weight.
4. Calculate the void volume (this will correspond in most cases to the air bubble that will travel through the package when the package is inverted from its original filling orientation):

| | |
|---|---|
| Water Volume | (Water Weight Ave. − Empty Weight Ave.)/Water sp. gr. |
| Composition Volume | (Comp. Weight Ave. − Empty Weight Ave)/Comp. sp. gr. |
| Void Volume % | 100*(Water Volume − Composition Volume)/Water Volume |

Note: use the same weight units for each weight measurement; sp. gr.=specific gravity.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

DETAILED DESCRIPTION OF THE INVENTION

As stated above, the invention relates to a process for making compositions with multiple liquid phases, a method for providing, and an article of commerce.

While many variations in the physical characteristics of the components are possible, i.e., color, rheology, texture, density etc, variations in color are widely sought. The specific design or pattern achieved (i.e., width, length of stripe or marbling etc.) in the combination product can be varied by varying a number of factors including, but not limited to rheological characteristics of the phases, diameter of the dispensing means, presence or absence of rotation of the container during filling, rate of speed and constancy.

Placement of the dispensing means during filling of these multiple liquid phase products is an additional process variable. In one embodiment, the process involves initially placing the nozzle near the bottom of the container to be filled and lifting the dispensing means as the container fills. In other variations, the container itself can be raised on the dispensing means, or the container can be filled from the top. In one possible variation, the container can be filled upside down and the bottom attached to the container following filling.

For embodiments where a non-lathering (lipid) phase is utilized in combination with a lathering phase, the lathering phase may require heating and passing through a heat exchanger for cooling prior to start of the combining/filling process.

In one embodiment of the invention the composition is dispensed from the container upon being hand squeezed or inverted to gravity feed the composition. In one embodiment, the process is used to produce a spirally striped personal cleansing composition having a first stripe comprising a lathering phase containing a surfactant, water, and optional conventional personal cleansing ingredients and at least one additional stripe comprising a separate non-lathering phase In one embodiment, one or more of the phases can include stable colorants, resulting in the possibility of visual patterns when the personal cleansing compositions are packaged in containers which allow the contents to be viewed.

These multiple liquid phase personal care compositions are processed so that the two separate phases are in physical contact yet remain stable. These compositions further provide improved aesthetics via the visually distinct (e.g., striped) appearance during and after application.

a. Liquid Compositions

Any suitable liquid compositions can be used in the practice of the invention herein. For instance, suitable liquid compositions can include shampoos, conditioners, foundations, washes, soaps, and the like. Preferably, the liquid compositions used to in making the personal care compositions herein have substantially the same density and/or rheology. Suitable examples of compositions that can be used herein include, but are not limited to, those disclosed in the "Background Art" section above.

In a preferred embodiment, at least two liquid compositions are used that are physically distinct, preferably visually distinct. In a particular embodiment, the visually distinct phases are of a different color. For instance, one or more phases can comprise a dye, pigment, pearlescent agent, lake, coloring, or mixtures thereof. Colorants useful in the present invention can be, for example, selected from the group consisting of Red 30 Low Iron, FD&C Red 40 AL Lake, D&C Red Lake Blend of Lake 27 & Lake 30, FD&C Yellow 5 Al Lake, FD&C Yellow 6 Al Lake, FD&C Yellow 5 Lake, FD&C Blue #1 AL Lake, Kowet Titanium Dioxide, D&C Red 30 Talc Lake, D&C Red 6 Barium Lake, D&C Red 7 Calcium Lake, D&C Red 34 Calcium Lake, D&C Red 30 AL lake, D&C Red 27 AL lake, D&C Yellow 10 AL lake, D&C Red 21 AL Lake, Yellow Iron Oxide, D&C Red 30 Lake, Octocir Yellow 6 AL Lake, Octocir Yellow 5 AL Lake, D&C Red 28 Lake, D&C Orange 5 Zirc Al Lake, Cos Red Oxide BC, Cos Iron Oxide Red BC, Cos Iron oxide Black BC, Cos Iron Oxide Yellow, Cos Iron Oxide Brown, Cos Iron Oxide Yellow BC, Euroxide Red Unsteril, Euroxide Black Unsteril, Euroxide Yellow Steril, Euroxide Black Steril, Euroxide Red, Euroxide Black, Hydrophobic Euroxide Black, Hydrophobic Euroxide Yellow, Hydrophobic Euroxide Red, D&C Yellow 6 Lake, D&C Yellow 5 Zr Lake, and mixtures thereof.

In one embodiment, the personal care composition comprises at least two physically distinct phases, wherein at least one phase has a average low shear rate viscosity of from about 25 to about 2000 Pascal-seconds, in another embodiment from about 50 to about 1500 Pascal-seconds, and still in another embodiment from about 75 to about 1000 Pascal-seconds.

b. Product Container

Any suitable product container can be used herein. In one embodiment, the container is a bottle. In another embodiment, the container is a bottle with a flat cap. In still another embodiment, the container is a tottle.

In a specific embodiment, a clear or opaque bottle is used. For instance, in a particular embodiment, the bottle is made from, for example, the bottle can be made from a polyolefin, such as polypropylene, polyethylene (e.g., linear low density, low density, high density, copolymers such as ethylene, vinyl, and acetate), polyethylene terephthalate and co-polymers, and nylon.

In one embodiment, the product container is a bottle that is filled from the same end from which the product is to be dispensed. In a particular embodiment, the end from which the bottle is filled is not only the end from which the product is to be dispensed, but it is also the end upon which the bottle is intended to rest or sit upon (e.g., the bottle's base) for storage by the consumer and/or for display on the store shelf (this bottle is referred to herein as a "tottle"). Typically, the closure on a tottle is flat or concave, such that the tottle, when stored, rests on the closure. In particular embodiments, the closure can be, for example, a cap, flip-top, screw-on, screw-on flip-top cap, rocker cap, etc.

In particular embodiments, a tottle can be a preferred container. If a tottle is used, the personal care composition can be stored with the end from which it was filled facing downward. This avoids the need to tip the bottle over to dispense product upon each usage by the consumer, thus eliminating the movement of air bubble(s) through the length of the product in the package upon each usage occasion by the consumer. Movement of air bubble(s) through the length of the product is undesirable from an aesthetic standpoint, as this can disrupt the attractive appearance of a product having visually distinct phases. This loss of product attractiveness undesirably detracts from the consumer's enjoyment of the product.

In yet another embodiment, the container is a bottle that can stand on either end in a upright position.

c. Filling the Empty Product Container to Form a Container of Personal Care Composition Having a Void Volume of from about 0% to about 4%

In one embodiment, the empty product container is filled with the liquid compositions to form a container of personal care composition having a void volume of from about 0% to about 4%, in another embodiment from about 0% to about 2%, and in still another embodiment from about 0% to about 2%. Such filling can comprise transferring predetermined amounts of a plurality of liquid compositions through at least one dispensing means into the empty product container.

Preferably, minimal void volume remains in the finished container of personal care composition. Minimizing the void volume can be accomplished through any suitable means. Such methods can include, but are not limited to, filling methods known in the art such as: (1) overfilling the container, followed by cleaning off the overfill; (2) topping off (e.g., by using a secondary filler, filling by hand, etc.); (3) using a container closure that displaces at least part of the void area (e.g., a deformable plug that occupies at least part of the void area); (4) utilizing a venting closure that allows the void (e.g., air bubble) to escape; and (5) carefully filling the container.

Any suitable method can be used to fill the container. For instance, those methods set forth in the "Background Art" section above can be used.

d. Curing

After filling, the composition can optionally undergo a curing step. During the curing step, the composition can be allowed to stabilize before shipping. For instance, the composition can be allowed to cool, crystallize, etc., before being shipped for consumer purchase.

e. Providing

The invention herein also provides a method for providing a stable, visually distinct, multiple liquid phase composition. This method comprises placing said container in a shipping package, wherein said container is placed in said shipping package in the same orientation at which it was filled. For example, if the container was filled in the up-right position, it is placed in the shipping package in the up-right position. This can help to maintain the desired aesthetic appearance of the multi-phase personal care product, as this can prevent the movement of air bubble(s) throughout the product, which can disrupt the product's visually distinct pattern. Furthermore, it can reduce the occurrence of leakage from the orifice of the closure.

Any suitable shipping package can be used herein. For instance, the shipping package can be a box or a container. In one embodiment, the package is a box comprising multiple spaces for containing multiple finished product packages for shipping to a destination for consumer purchase.

f. Optionally Turning for Storage

In one embodiment, the personal care composition is stored, either on a store shelf and/or by a consumer, in an orientation that is opposite to that which it was filled.

g. Article of Commerce

In another aspect, the present invention provides an article of commerce providing a container and a personal care composition. In a particular composition, the article of commerce comprises:

a. a bottle; and
  b. a personal care composition contained within said bottle, wherein said personal care composition comprises at least two physically distinct phases, and further wherein said personal care composition has an average low shear rate viscosity of from about 25 to about 2000 Pascal-seconds in at least one phase.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Each of the exemplified compositions provides improved deposition or effectiveness of the skin conditioning agents or optional ingredients delivered from each prepared composition.

The following examples described in Table 1 are non-limiting examples of the personal cleaning compositions herein.

| | Example 1 | Example 2 | Example 3 | Example 4 |
|---|---|---|---|---|
| Phase 1 | | | | |
| Ammonium Laureth-3 Sulfate | 10 | | | |
| Ammonium Lauryl Sulfate | 6 | | | |
| Sodium Laureth-3 Sulfate | | 12 | 12 | 12 |
| Sodium Lauryl Sulfate | | 2 | 2 | 2 |
| Cocamidopropyl Betaine | | 2 | 2 | 2 |
| Coconutmonoethanol amide (CMEA, Mona Industries) | 0.8 | 2 | 2 | 2 |
| Cetyl alcohol | 0.6 | 0 | 0 | 0 |
| Ethylene Glycol Distearate (EGDS) | 1.5 | | | |
| Carbopol Aqua SF-1 (30%) (Noveon) | 2 | 2 | 1 | |
| Keltrol CGT (Xanthan Gum from Kelco) | | | | 3 |
| Polyquaterium 10, (UCARE polymer JR-30M from Amerchol) | | | 0.25 | 0.25 |
| Polymethacrylamidopropyltrimonium Chloride (Polycare 133 from Rhodia) | 0.13 | | | |
| Dimethicone (Viscasil 330M from General Electric) | 2 | | | |
| Kathon CG (Rhom & Haas) | 0.0005 | 0.0005 | 0.0005 | 0.0005 |
| Disodium EDTA (Dissolvine NA-2S, Akzo Nobel) | 0.1274 | 0.1274 | 0.1274 | 0.1274 |
| Sodium chloride (Morton) | 0.7 | 0.5 | 0.5 | 0.5 |
| Sodium Citrate Dihydrate | 0.4 | 0.4 | 0.4 | 0.4 |
| Citric Acid (Hoffman-Laroche) | 0.15 | 0.15 | 0.15 | 0.15 |
| Perfume | 0.6 | 0.6 | 0.6 | 0.6 |
| Water | q.s. | q.s. | q.s. | q.s. |
| Phase 2 | | | | |
| Ammonium Laureth-3 Sulfate | 10 | | | |
| Ammonium Lauryl Sulfate | 6 | | | |
| Sodium Laureth-3 Sulfate | | 12 | 12 | 12 |
| Sodium Lauryl Sulfate | | 2 | 2 | 2 |
| Cocamidopropyl Betaine | | 2 | 2 | 2 |
| Coconutmonoethanol amide (CMEA, Mona Industries) | 0.8 | 2 | 2 | 2 |
| Cetyl alcohol | 0.6 | 0 | 0 | 0 |
| Ethylene Glycol Distearate (EGDS) | 1.5 | | | |
| Carbopol Aqua SF-1 (30%) (Noveon) | 2 | 2 | 2 | |
| Keltrol CGT (Xanthan Gum from Kelco) | | | | 3 |
| Polyquaterium 10, (UCARE polymer JR-30M from Amerchol) | | | 0.25 | 0.25 |
| Polymethacrylamidopropyltrimonium Chloride (Polycare 133 from Rhodia) | 0.13 | | | |
| Dimethicone (Viscasil 330M from General Electric) | 2 | | | 2 |
| Kathon CG (Rhom & Haas) | 0.0005 | 0.0005 | 0.0005 | 0.0005 |
| Disodium EDTA (Dissolvine NA-2S, Akzo Nobel) | 0.1274 | 0.1274 | 0.1274 | 0.1274 |
| Sodium chloride (Morton) | 0.7 | 0.5 | 0.5 | 0.5 |
| Sodium Citrate Dihydrate | 0.4 | 0.4 | 0.4 | 0.4 |
| Citric Acid (Hoffman-Laroche) | 0.15 | 0.15 | 0.15 | 0.15 |
| D &C Red # 30 Talc Lake | 0.02 | 0.02 | 0.02 | 0.02 |
| Perfume | 0.6 | 0.6 | 0.6 | 0.6 |
| Water | q.s. | q.s. | q.s. | q.s. |

Cleansing Phase Compositions:

In an appropriate vessel, add distilled water and stir at an appropriate speed (100-200 ppm) using an appropriate sized stir blade. If needed, add the anionic polymer (Carbopol Aqua SF-1), cationic polymers (Polyquaternium-10, Polycare 133) and stir briefly and slowly to wet and disperse the polymer. While continuing to stir, if needed, add the citiric acid solution (50%) drop wise to the mix vessel to reduce pH until solution becomes clear. Add surfactants (AS, AES, and CAPB,) to the mixture. Heat the mixture to 60° C. and while stirring add CMEA, EGDS, and Cetyl alcohol to the mixture. Mix until homogeneous. Cool the solution to room temperature while stirring and add Dimethicone, EDTA, Mackstat DM-C, D&C pigment, and perfume. Finally, adjust pH of the product within the preferred specified range of from about 5.5 to about 6.5.

All documents cited herein are incorporated herein by reference in their entirety. The citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a stable personal care composition, said personal care composition having multiple liquid phases in physical contact that remain visually distinct for about 30 days at ambient conditions without agitation, wherein said process comprises the steps of:
   a. placing a plurality of liquid compositions in separate vessels equipped with at least one dispensing means for transferring said compositions from said vessels, wherein said liquid compositions are physically distinct from one another;
   b. providing an empty product container, wherein said empty product container is a tottle, wherein said tottle comprises:
   a product-filling end;
   a base for resting upon when stored or displayed, where said base is located at the same end of the tottle as said product-filling end; and
   c. filling said empty product container with said liquid compositions, such that said liquid compositions are in physical contact with one another wherein said liquid compositions comprise an average low shear rate viscosity of from about 25 to about 2000 Pascal-seconds in at least one phase, to form a container of said personal care composition having a void volume of from about 0% to about 4%, wherein said filling step comprises transferring predetermined amounts of said liquid compositions through at least one said dispensing means into said empty product container.

2. A process for making a stable, physically distinct, multiple liquid phase personal care composition, said personal care composition having multiple liquid phases in physical contact that remain visually distinct for about 30 days at ambient conditions without agitation, wherein said process comprises the steps of:
   a. placing a plurality of liquid compositions in separate vessels equipped with at least one dispensing means for transferring said compositions from said vessels, wherein said liquid compositions are physically distinct from one another;
   b. providing an empty product container, wherein said empty product container is a tottle, wherein said tottle comprises:
   a product-filling end;
   a base for resting upon when stored or displayed, where said base is located at the same end of the tottle as said product-filling end; and
   c. filling said empty product container with said liquid compositions, such that said liquid compositions are in physical contact with one another wherein said liquid compositions comprise an average low shear rate viscosity of from about 25 to about 2000 Pascal-seconds in at least one phase, to form a container of said personal care composition having a void volume of from about 0% to about 4%, wherein said filling step comprises transferring predetermined amounts of said liquid compositions through at least one said dispensing means into said empty product container;
   d. curing said personal care composition, wherein said curing step comprises maintaining said product container in the same orientation in which it was filled until the desired level of cure is reached; and
   e. placing said container in a shipping package, wherein said container is placed in said shipping package in the same orientation at which it was filled.

* * * * *